United States Patent
Matsumoto et al.

(10) Patent No.: US 8,765,296 B2
(45) Date of Patent: Jul. 1, 2014

(54) IONIC LIQUID

(75) Inventors: Hajime Matsumoto, Ikeda (JP); Naohiro Terasawa, Ikeda (JP); Seiji Tsuzuki, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 469 days.

(21) Appl. No.: 12/991,577

(22) PCT Filed: May 1, 2009

(86) PCT No.: PCT/JP2009/058581
§ 371 (c)(1),
(2), (4) Date: Nov. 8, 2010

(87) PCT Pub. No.: WO2009/136609
PCT Pub. Date: Nov. 12, 2009

(65) Prior Publication Data
US 2011/0091769 A1    Apr. 21, 2011

(30) Foreign Application Priority Data
May 9, 2008  (JP) .................................. 2008-123630

(51) Int. Cl.
*H01M 6/04* (2006.01)
*H01G 9/02* (2006.01)
*C08G 79/08* (2006.01)

(52) U.S. Cl.
USPC ............................. 429/199; 252/62.2; 528/6

(58) Field of Classification Search
None
See application file for complete search history.

(56) References Cited

U.S. PATENT DOCUMENTS

| | | | |
|---|---|---|---|
| 2003/0099802 A1* | 5/2003 | Klun et al. ................... | 428/64.1 |
| 2006/0181835 A1* | 8/2006 | Murakami et al. ............ | 361/503 |
| 2007/0099079 A1 | 5/2007 | Matsumoto et al. | |
| 2008/0008930 A1* | 1/2008 | Matsumoto et al. .......... | 429/122 |

FOREIGN PATENT DOCUMENTS

| | | |
|---|---|---|
| JP | 2002-099001 A | 4/2002 |
| JP | 2003-331918 A | 11/2003 |
| WO | 2005/063773 A1 | 7/2005 |

OTHER PUBLICATIONS

Terasawa, Naohiro et al "Physical and electrochemical properties of new ionic liquids based on [CF3OCF2CF2BF2]," The Electrochemical Society of Japan, Mar. 29, 2009, p. 248.
Frohn, Hermann-Josef and Bardin, Vadim V. "The unusual reactivity of C3F7OCF=CF2 with PBu3 and the complex hydrides M[EH4] (M: Li, Na; E: B, Al); preparation of potassium perfluoro-2-propoxyeth-1-enyltrifluoroborate K [C3F7OCF=CFBF3]," Journal of Fluorine Chemistry, Feb. 14, 2003, vol. 123, pp. 43-49.
International Search Report of PCT/JP2009/058581, mailing date Jun. 2, 2009.
Terasawa, N. et al., "Alkoxy chains in ionic liquid anions; effect of introducing ether oxygen into perfluoroalkylborate on physical and thermal properties", Chem. Commun., 40, p. 1730-1732 (2010).
Forsyth, S. A. et al., "N-methyl-N-alkylpyrrolidinium nonafluoro-1-butanesulfonate salts: Ionic liquid properties and plastic crystal behaviour", Green Chem, 8, p. 256-261 (2006).
Zhou, Z, et al. "Cyclic Quaternary Ammonium Ionic Liquids with Perfluoroalkyltrifluoroborates: Synthesis, Characterization, and Properties", Chemistry European Journal, 12, p. 2196-2212 (2006).
Zhou, Z. et al., "Low-Melting, Low-Viscous, Hydrophobic Ionic Liquids: 1-Alkyl(Alkyl Ether)-3-methylimidazolium Perlluoroalkyltrifluoroborate", Chemistry European Journal, 10, p. 6581-6591 (2004).
Matsumoto, H. "Thermal and Physical Properties of N,N-diethyl-N-methyl-N-propylammonium salts", AIST, p. 1.
Bonhôte, P. et al., "Hydrophobic, Highly Conductive Ambient-Temperature Molten Salts", Inorganic Chemistry, vol. 35, No. 5, p. 1168-1178 (1996).

* cited by examiner

*Primary Examiner* — Milton I Cano
*Assistant Examiner* — Sarah A Slifka
(74) *Attorney, Agent, or Firm* — Westerman, Hattori, Daniels & Adrian, LLP

(57) ABSTRACT

Disclosed is an ionic liquid having a low melting point, a low viscosity, and high electrical conductivity. Specifically disclosed is an anion represented by $[CF_3OCF_2CF_2BF_3]^-$ for use in the production of such ionic liquids.

13 Claims, No Drawings

IONIC LIQUID

This application is a national stage entry of PCT Application No. PCT/JP2009/058581 filed May 1, 2009 and claiming priority to Japanese application number 2008-123630 filed May 9, 2008.

TECHNICAL FIELD

The present invention relates to ionic liquids, and more particularly to ionic liquids with low viscosities, low melting points, and high electrical conductivities. The present invention also relates to lithium batteries (particularly lithium secondary batteries), dye-sensitized solar cells, and electric double-layer capacitors comprising the ionic liquids.

BACKGROUND ART

Ionic liquids have attracted special attention for the past several years, owing to their potential uses as electrolytes for a variety of electrochemical devices such as lithium secondary batteries, solar cells, actuators, electric double-layer capacitors and the like, reaction media, and catalysts for organic syntheses. Compared with conventional organic liquid electrolytes, the main advantages of ionic liquids as electrolytes are flame retardance, non-volatility and high thermal stability. Bistrifluoromethylsulfonylimide ($[(CF_3SO_2)_2N]^-$) and tetrafluoroborate ($BF_4^-$) have attracted attention as anions for most of the ionic liquids reported thus far, because of their high electrochemical stabilities and thermal stabilities (PTL 1 and PTL 2).

Moreover, anions represented by $[(nC_nF_{2+1})BF_3]^-$ (wherein n is 1, 2, 3, or 4) of ionic liquids are also known (PTL 3).

However, ionic liquids containing these anions have suffered from problems such as, in particular, low conductivities at low temperatures.

CITATION LIST

Patent Literature

PTL 1: Japanese Unexamined Patent Publication No. 2002-099001
PTL 2: Japanese Unexamined Patent Publication No. 2003-331918
PTL 3: Japanese Unexamined Patent Publication No. 2005-063773

SUMMARY OF INVENTION

Technical Problem

An object of the present invention is to provide ionic liquids with low viscosities, low melting points, and high electrical conductivities by improving the anionic components.

Solution to Problem

In view of the aforementioned problems, the present inventors conducted extensive research, and found that an ionic liquid with a low viscosity, a low melting point, and a high electrical conductivity at low temperatures can be obtained by using an anion represented by $[CF_3OCF_2CF_2BF_3]^-$, or solid salts containing the anion.

More specifically, the present invention provides ionic liquids and anions therefor, a method of producing the ionic liquids, and capacitors using the ionic liquids, as itemized below:

Item 1. An anion represented by $[CF_3OCF_2CF_2BF_3]^-$ for use in the production of ionic liquids.
Item 2. An ionic liquid comprising an anion represented by $[CF_3OCF_2CF_2BF_3]^-$ and at least one organic onium ion.
Item 3. A lithium battery comprising the ionic liquid according to Item 2.
Item 4. An electric double-layer capacitor comprising the ionic liquid according to Item 2.
Item 5. A method of producing an ionic liquid, comprising mixing a compound containing $[CF_3OCF_2CF_2BF_3]^-$ as an anion component, with a compound containing at least one organic onium compound.

Advantageous Effects of Invention

The ionic liquids of the present invention are suitable for use in electrochemical devices such as lithium secondary batteries, fuel cells, solar batteries, electrical double-layer capacitors and the like, as solvents for chemical reactions, and as lubricants.

DESCRIPTION OF EMBODIMENTS

The ionic liquids for use in the invention typically have melting points of 100° C. or less, preferably 65° C. or less, more preferably 45° C. or less, still more preferably 25° C. or less, and even more preferably 0° C. or less. For example, ionic liquids with melting points of 100° C. or less can find a wide range of uses in fuel cells. On the other hand, ionic liquids for use in energy devices, such as solar cells, lithium batteries, and capacitors; electrochromic devices; and electrochemical devices, such as electrochemical sensors, preferably have melting points of room temperature (25° C.) or less, and more preferably 0° C. or less.

When the ionic liquids for use in the invention have melting points that cannot be clearly observed, the ionic liquids, as long as they have glass transition temperatures of −20° C. or less, preferably −50° C. or less, more preferably −80° C. or less, and still more preferably −100° C. or less, can be handled in the same manner as those having melting points in the same temperature range.

In the invention, an anion represented by $[CF_3OCF_2CF_2BF_3]^-$ is used as an anion component of an ionic liquid. This anion is a novel compound and can be obtained as follows: PhMgBr is added dropwise to a stirred solution of $CF_3OCF_2CF_2I$ in anhydrous $Et_2O$ under $N_2$ atmosphere at −78° C. for 1 hour. After further stirring at −78° C., $B(OCH_3)_3$ is added, and the reaction mixture is continuously stirred at −78° C. for 2 hours, followed by warming to room temperature. The obtained suspension is poured into 100 ml of a 48% aqueous HF solution that has been previously cooled to 0° C., and the mixed solution is vigorously stirred overnight. After saturation with KF at 0° C., the ether phase is separated and dried, and the solvent is distilled off, followed by recrystallization.

The ionic liquid can be produced by mixing an organic onium compound with a salt of an anionic component represented by $[CF_3OCF_2CF_2BF_3]^-$ and a cationic component, such as an alkali metal ion ($Na^+$, $K^+$, $Li^+$, $Cs^+$, etc.), an alkaline-earth metal ion ($Ca^{2+}$, $Mg^{2+}$, $Ba^{2+}$, etc.), $H^+$, and $Bu_3Sn^+$; and separating an ionic liquid consisting of the organic onium ion and $[CF_3OCF_2CF_2BF_3]^-$. For example, an ionic liquid consisting of $[CF_3OCF_2CF_2BF_3]^-$ and an organic onium ion can be preferably obtained by mixing an (organic onium)⁺(OH)⁻ salt with a [CF₃OCF₂CF₂BF₃]⁻H⁺ salt, which is prepared by passing through an ion exchange resin; and removing water. A salt-exchange reaction for obtaining an ionic liquid can be carried out by solvent extraction when the desired molten salt is capable of being extracted.

Examples of organic onium ions include ammonium, guanidinium, phosphonium, oxonium, and sulfonium. Among these examples, ammonium, guanidinium, phosphonium, and sulfonium are preferable; ammonium, guanidinium, and phosphonium are more preferable; and ammonium is still more preferable.

Although an organic onium ion may be used singly, a combination of two or more organic onium ions can further reduce the melting point and viscosity of the resulting ionic liquid.

Moreover, although [CF₃OCF₂CF₂BF₃]⁻ is used as the anion of the ionic liquid, the anion may be used together with other anion(s), as long as [CF₃OCF₂CF₂BF₃]⁻ is a principal component.

Examples of each organic onium compound are listed below:

(1) Ammonium represented by the formula (Ia) or (Ib)

$$[R^4—NR^1R^2R^3]^+ \quad (Ia)$$

[Chem. 1]

(Ib)

In the formulae (Ia) and (Ib), each of R¹, R² and R³, which may be the same or different, is a hydrogen atom, an alkyl group, a haloalkyl group, an alkoxy group, an alkylthio group, a polyether group, an optionally substituted aryl group, an optionally substituted aralkyl group, an alkoxyalkyl group, or a heterocyclic group. In the formula (Ia), R¹ and R², taken together with the nitrogen atom, may form an optionally substituted 5- to 8-membered nitrogen-containing heterocyclic group.

R⁴ is an alkyl group, a haloalkyl group, an alkoxy group, a polyether group, an optionally substituted aryl group, an optionally substituted aralkyl group, or an alkoxyalkyl group; an organic functional group having redox properties; or a group derived from a volatile organic solvent.

(2) Guanidinium represented by the formula (Ic)

[Chem. 2]

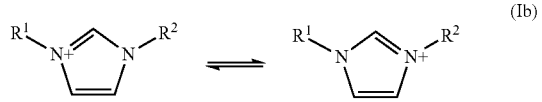
(Ic)

wherein R¹ and R² are the same as defined in the formula (Ia).

(3) Phosphonium represented by the formula (Id)

$$[R^4—PR^1R^2R^3]^+ \quad (Id)$$

wherein R¹, R², R³, and R⁴ are the same as defined in the formula (Ia); provided that R¹ and R², taken together with the phosphorus atom, may form an optionally substituted 5- to 8-membered phosphorus-containing heterocyclic group.

(4) Oxonium represented by the formula (Ie)

$$[R^4—OR^1R^2]^+ \quad (Ie)$$

wherein R¹, R², and R⁴ are the same as defined in the formula (Ia); provided that R¹ and R², taken together with the oxygen atom, may form an optionally substituted 5- to 8-membered oxygen-containing heterocyclic group.

(5) Sulfonium represented by the formula (If)

$$[R^4—SR^1R^2]^+ \quad (If)$$

wherein R¹, R², and R⁴ are the same as defined in the formula (Ia); provided that R¹ and R², taken together with the sulfur atom, may form an optionally substituted 5- to 8-membered sulfur-containing heterocyclic group.

Examples of organic onium compounds include salts of organic onium cations with halogen ions, nitrate ions, sulfate ions, phosphate ions, perchlorate ions, methanesulfonate ions, toluenesulfonate ions, and like ions.

Alternatively, the ionic liquid may be produced using an anion (in the form of, for example, a silver salt, a calcium salt or a barium salt) represented by [CF₃OCF₂CF₂BF₃]⁻ and an organic onium ion (in the form of, for example, a halide salt or a sulfate salt) to form a sparingly soluble salt, such as a silver halide, barium sulfate or calcium sulfate resulting from the aforementioned counter-ions; and removing the formed salt.

Examples of alkyl groups include $C_{1-20}$ straight or branched alkyl groups, such as methyl, ethyl, n-propyl, isopropyl, n-butyl, sec-butyl, isobutyl, t-butyl, pentyl, hexyl, heptyl, octyl, nonyl, decyl, undecyl, dodecyl, tridecyl, tetradecyl, hexadecyl, octadecyl, eicosyl, and the like.

Examples of haloalkyl groups include $C_{1-20}$ haloalkyl groups resulting from the substitution of at least one hydrogen atom of any of the aforementioned alkyl groups with a halogen atom (chlorine, bromine, fluorine or iodine), and preferably with a fluorine atom.

Examples of alkoxy groups include $C_{1-20}$ straight or branched alkoxy groups with the structure [O-an alkyl mentioned above].

Examples of alkylthio groups include $C_{1-20}$ straight or branched alkoxy groups with the structure [S-an alkyl mentioned above].

Examples of aryl groups include $C_{6-14}$ aryl groups such as phenyl, toluoyl, xylyl, ethylphenyl, 1,3,5-trimethyl phenyl, naphthyl, anthranil, phenanthryl, and like groups.

Examples of aralkyl groups include $C_{7-15}$ aralkyl groups such as benzyl, phenethyl, and naphthylmethyl groups.

The alkoxy and alkyl groups of alkoxyalkyl groups are the same as mentioned above. Examples of alkoxyalkyl groups include $C_{1-20}$ straight or branched alkyl groups substituted with $C_{1-20}$ straight or branched alkoxy groups. Preferable examples among them are methoxymethyl (—CH₂OCH₃), methoxyethyl (—CH₂CH₂OCH₃), ethoxymethyl (—CH₂OCH₂CH₃), and ethoxyethyl (—CH₂CH₂OCH₂CH₃) groups.

Examples of polyether groups include polyether groups represented by —(CH₂)$_{n1}$—O—(CH₂CH₂O)$_{n2}$—(C₁-C₄ alkyl) or —(CH₂)$_{n1}$—O—(CH₂CH(CH₃)O)$_{n2}$— (C₁-C₄ alkyl), wherein n1 is an integer of 1 to 4; n2 is an integer of 1 to 4; and the C₁-C₄ alkyl is, for example, methyl, ethyl, n-propyl, isopropyl, n-butyl, isobutyl, sec-butyl, or tert-butyl.

Moreover, R¹ and R², taken together with the nitrogen atom linked to them, may form a 5- to 8-membered, and preferably a 5- or 6-membered, nitrogen-containing heterocyclic group (pyrrolidinium, piperidinium, pyrrolinium, pyridinium, or the like).

Examples of substituents for aryl and aralkyl groups include halogen atoms (F, Cl, Br and I), hydroxy groups, methoxy groups, nitro groups, acetyl groups, acetylamino groups and the like. The aforementioned alkyl groups or alkenyl groups may have one or more of —O—, —COO— and —CO— interposed between C—C single bonds at any positions to form ether, ester, or ketone structures.

Specific examples of ionic liquids prepared using the organic onium compounds represented by the formula (I), wherein $R^4$ is an organic functional group having redox properties, are compounds according to the following formulae (II) to (VIII):

[Chem. 3]

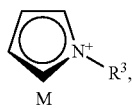
(II)

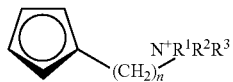
(III)

wherein n is 0 or 1; M is a transition metal; each of $R^1$, $R^2$ and $R^3$, which may be the same or different, is an alkyl group, a haloalkyl group, an alkoxy group, an optionally substituted aryl group, an optionally substituted aralkyl group or an alkoxyalkyl group; and $R^1$ and $R^2$, taken together with the nitrogen atom, may form a 5- to 8-membered nitrogen-containing cyclic group.

[Chem. 4]

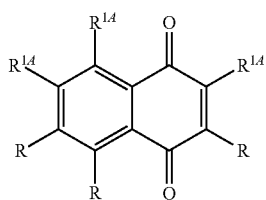
(IV)

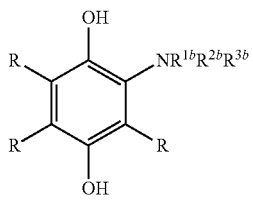
(V)

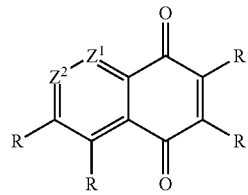
(VI)

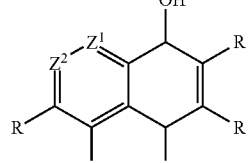
(VIa)

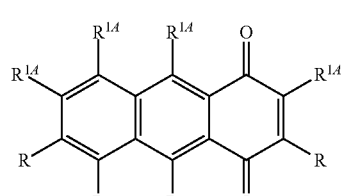
(VII)

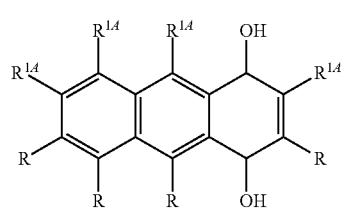
(VIIa)

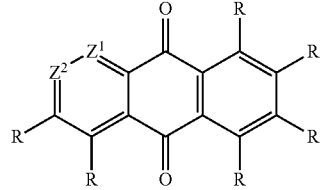
(VIII)

wherein each of the Rs, which may be the same or different, is a halogen atom, an alkyl group, an alkoxy group, an alkanoyl group, a hydroxy group, a carboxyl (COOH) group, an alkoxycarbonyl group, a nitro group, a cyano (CN) group, an acetylamino group, a phenyl group, a benzyl group or a perfluoroalkyl group; alternatively, two adjacent Rs, taken together with the carbon atoms linked to them, may form a benzene ring.

One of the plurality of $R^{1A}$s is $NR^{1b}R^{2b}R^{3b}$, and each of the other $R^{1A}$s, which may be the same or different, is an R; each of $R^{1b}$, $R^{2b}$ and $R^{3b}$, which may be the same or different, is an alkyl group, a haloalkyl group, an alkoxy group, an optionally substituted aryl group, an optionally substituted aralkyl group or an alkoxyalkyl group; provided that $R^{1b}$ and $R^{2b}$, taken together with the nitrogen atom, may form a 5- to 8-membered nitrogen-containing cyclic group.

One of $Z^1$ and $Z^2$ is CH, and the other is $N^+$—$R^3$, wherein $R^3$ is as defined above.

M represents a transition metal atom, examples of which include Fe, Co, Ni, Zn, Cu, Cr, V, Cd, As, Mn, Ti, Zr, Sn, Ag, In, Hg, W, Pt, Au, Ga, Ge and Ru; a preferable example being Fe.

Examples of halogen atoms include chlorine, fluorine, bromine and iodine atoms.

Examples of alkanoyl groups include $C_{2-21}$ straight or branched alkanoyl groups represented by the formula: —CO-(alkyl), wherein the alkyl is as defined above, such as acetyl, propionyl, butyryl and the like.

Examples of alkoxycarbonyl groups include $C_{2-21}$ straight or branched alkoxycarbonyl groups represented by the formula: —CO—O(alkyl), wherein the alkyl is as defined above, such as methoxycarbonyl, ethoxycarbonyl, butoxycarbonyl and the like.

Examples of perfluoroalkyl groups include groups in which all of the hydrogen atoms of any of the aforementioned alkyl groups are substituted with fluorine atoms, such as groups represented by $C_nF_{2n+1}$, wherein n is an integer of 1 to 20.

A cationic group in which $R^4$ is a group derived from a volatile organic solvent is introduced into an organic solvent via an alkylene group, as necessary. Examples of organic solvents include compounds that are solid or liquid at room temperature, with boiling points of −100 to 300° C., and preferably 30 to 300° C., at atmospheric pressure. Specific examples of such compounds are as follows.

Ethers: diethyl ether, tetrahydrofuran, tetrahydropyrane, diisopropyl ether, diphenyl ether, anisole, phenetole, guaiacol, etc.

Alkylene glycols: ethylene glycol, propylene glycol, butylene glycol, diethylene glycol, triethylene glycol, etc.

Alkylene glycol monoalkyl ethers: ethylene glycol monomethyl ether, ethylene glycol monoethyl ether, propylene glycol monomethyl ether, propylene glycol monoethyl ether, butylene glycol monomethyl ether, butylene glycol monoethyl ether, diethylene glycol monomethyl ether, diethylene glycol monoethyl ether, etc.

Alkylene glycol dialkyl ethers: ethylene glycol dimethyl ether (DME), ethylene glycol diethyl ether, propylene glycol dimethyl ether, propylene glycol diethyl ether, butylene glycol dimethyl ether, butylene glycol diethyl ether, diethylene glycol dimethyl ether, diethylene glycol diethyl ether, etc.

Esters: methyl acetate, ethyl acetate, propyl acetate, butyl acetate, methyl propionate, ethyl propionate, propyl propionate, butyl propionate, methyl formate, ethyl formate, propyl formate, butyl formate, methyl benzoate, ethyl benzoate, propyl benzoate, butyl benzoate, etc.

Lactones: γ butyrolactone (GBL), etc.

Ketones: acetone (ATN), acetylacetone, methyl ethyl ketone, cyclohexanone, cyclopentanone, etc.

Heteroaromatic hydrocarbons: pyridine, etc.

Alicyclic hydrocarbons: cyclopentane, cyclohexane, methylcyclohexane, etc.

Heteroalicyclic compounds: dioxane, morpholine, pyrrolidine, etc.

Sulfides: dimethyl sulfide, diethyl sulfide, di-n-propylsulfide, diisopropylsulfide, etc.

Carbonates: ethylene carbonate (EC), propylene carbonate (PC), butylene carbonate, diethyl carbonate (DEC), dimethyl carbonate, etc.

Alcohols: ethanol, n-propanol, isopropanol, n-butanol, isobutanol, sec-butanol, tert-butanol, etc.

The above-described cationic group may be introduced into any of these organic solvents by, for example, the processes illustrated below:

[Chem. 5]

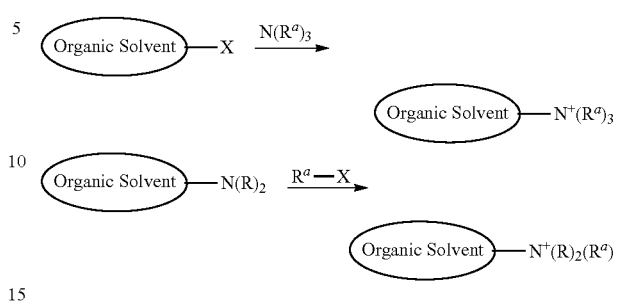

wherein the organic solvent is any of the aforementioned organic solvents; each of the $R^a$s is an optionally substituted alkyl group; R is a hydrogen atom or an optionally substituted alkyl group; and X is a leaving group.

Examples of an optionally substituted alkyl group represented by R or $R^a$ include $C_{1-3}$ alkyl groups such as methyl, ethyl, n-propyl, and isopropyl groups; and such an alkyl group may be substituted with a fluorine atom, a methoxy group, a cyano group or a similar group.

X represents a leaving group, and specific examples thereof include a chlorine atom, bromine atom, iodine atom, methane sulfonyl group, p-toluene sulfonyl group, and the like.

In one preferred embodiment of the invention, a quaternary ammonium group is introduced into a highly volatile solvent with a low boiling point, so as to form an ionic liquid. In order to produce a quaternary ammonium compound, a leaving group and a tertiary amine may be reacted as explained above, or the amino group of a solvent containing an amino group may be quaternized.

The cationic components mentioned above may be used singly or in combination. When used in combination, the proportion of such cationic components may be set as desired.

Examples of organic onium ions suitable for use in the invention are as follows:

Symmetric ammonium cations: tetramethylammonium, tetraethylammonium, tetrapropylammonium cations, etc.

Ammonium cations in which the shortest substituent has carbon atoms of at least 50% and less than 100% of those of the longest substituent (hereinafter also referred to as "pseudo-symmetric"): ethyltrimethylammonium, vinyltrimethylammonium, triethylmethylammonium, triethylpropylammonium, diethyldimethylammonium, tributylethylammonium, triethylisopropylammonium, butyldiethylmethylammonium (N1224), N,N-dimethylpyrrolidinium, N-methyl-N-ethylpyrrolidinium, N-methyl-N-propylpyrrolidinium (Py13), N-methyl-N-butylpyrrolidinium, N-methyl-N-ethylpiperidinium, N-methyl-N-piperidinium, N-methyl-N-butylpiperidinium, triethylmethoxymethylammonium, dimethylethylmethoxyethylammonium, dimethylethylmethoxymethylammonium, diethylmethylmethoxyethylammonium (DEME), diethylmethylmethoxymethylammonium cations, etc.

Asymmetric ammonium cations: trimethylpropylammonium, trimethylisopropylammonium, butyltrimethylammonium, allyltrimethylammonium, hexyltrimethylammonium, octyltrimethylammonium, dodecyltrimethylammonium, triethylmethoxyethoxymethylammonium, dimethyldipropylammonium cations, etc.

Divalent ammonium cations: hexamethonium cations, etc.

Symmetric imidazolium cations: 1,3-dimethylimidazolium, 1,3-diethylimidazolium, 1,3-dipropylimidazolium, 1,3-dipropylimidazolium cations, etc.

Asymmetric imidazolium cations: 1-ethyl-3-methylimidazolium, 1-methyl-3-propylimidazolium, 1-isopropyl-3-propylimidazolium, 1-tert-butyl-3-isopropylimidazolium cations, etc.

Pyridinium cations: N-ethylpyridinium, N-butylpyridinium cations, etc.

Symmetric sulfonium cations: trimethylsulfonium, triethylsulfonium, tributylsulfonium cations, etc.

Pseudo-symmetric sulfonium cations: diethylmethylsulfonium cations etc.

Asymmetric sulfonium cations: dimethylpropylsulfonium, dimethylhexylsulfonium, etc.

Symmetric phosphonium cations: tetramethylphosphonium, tetraethylphosphonium, tetrapropylphosphonium, tetrabutylphosphonium, tetraoctylphosphonium, tetraphenylphosphonium cations, etc.

Pseudo-symmetric phosphonium cations: trimethylethylphosphonium, triethylmethylphosphonium cations, etc.

Asymmetric phosphonium cations: hexyltrimethylphosphonium, trimethyloctylphosphonium cations, etc.

EXAMPLES

The present invention is described in more detail below with reference to examples.

Example 1

Method $^1$H NMR (500.2 MHz), $^{19}$F NMR (470.6 MHz), and $^{11}$B NMR (160.5 MHz) spectra were measured using a JEOL ECA-500 FT-NMR spectrometer for identification of compounds.

Density:

The density of an ionic liquid was determined by measuring the weight of 1.0 mL of ionic liquid three times at 25° C.

Specific Conductivity):

The ionic conductivity (K) of a neat (solvent-free) ionic liquid was measured in a sealed conductivity cell using a conductivity meter (Radiometer Analytical, model CDM230).

Viscosity:

The viscosity was measured using 0.6 mL of sample at 25° C. by a viscometer (Brookfield model DV-III+).

Thermogravimetric Analysis (TGA):

TGA was conducted using a thermal analysis system (Seiko Instruments, TG/DTA 6200). A sample with an average weight of 5 mg was placed in a platinum pan and heated to about 40 to 600° C. at a rate of 10° C./min in a nitrogen flow. The initiation of degradation was defined as a decomposition temperature ($T_d$).

Differential Scanning Calorimetry (DSC):

DSC was conducted using a thermal analysis system (Perkin Elmer, Pyris 1) attached with liquid nitrogen low-temperature controlling equipment. A sample with an average weight of 5 mg was sealed in a seal-type platinum pan and scanned at range of about −150 to 250° C. at a rate of 10° C./min in a helium flow. As for samples that showed only glass transition points but did not show melting points under these measurement conditions, only the glass transition points were described (Tg only); however, the results are consistently based on the aforementioned measurement conditions, and there may be the possibility that the samples will show melting points under different measurement conditions.

Synthesis

All of the starting materials used were commercial products, and were used without purification.

$K[CF_3OCF_2CF_2BF_3]$

PhMgBr (3.0 M in $Et_2O$; 17.5 ml) was added dropwise to a stirred solution of $CF_3OCF_2CF_2I$ (15.8 g, 50.7 mmol) in 300 ml anhydrous $Et_2O$ under $N_2$ atmosphere at −78° C. for 1 hour. After stirring at −78° C. for 1.5 hours, $B(OCH_3)_3$ (6.2 g, 60 mmol) was added over 10 minutes. The reaction mixture was continuously stirred at −78° C. for 2 hours, followed by warming to room temperature over 2 hours. The obtained suspension was poured into 100 ml of a 48% aqueous HF solution that had been previously cooled to 0° C., and the mixture was vigorously stirred overnight. After saturation with KF at 0° C., the ether phase was separated, and the aqueous phase was extracted with $Et_2O$. The combined ether extract was washed with an aqueous $KHCO_3$ solution and dried. The solvent was removed under vacuum, followed by recrystallization from $MeOH/CHCl_3$, thereby obtaining the title compound (7.7 g, 52.0%).

$^{19}$F NMR ($CD_3OD$, $CFCl_3$, 470.6 MHz) δ −54.9 (t, J=10.8 Hz, 3F), −88.4 (s, 2F), −136.4 (q, J=19.5 Hz, 2F), −154.3 (q, J=40.0 Hz, 3F); $^{11}$B NMR ($CD_3OD$, $H_3BO_3$, 160.5 MHz) δ −19.8 (m, 1B); MS m/z (%) 253 (100) $[CF_3OCF_2CF_2BF_3]^-$, 545 (100) $[2M-K]^-$;

$EMI[CF_3OCF_2CF_2BF_3]$ 1-ethyl-3-methylimidazolium chloride (EMICl) (0.54 g, 3.7 mmol) was added to a stirred aqueous solution (35 ml) of $K[CF_3OCF_2CF_2BF_3]$ (1.10 g, 3.8 mmol) at room temperature. The reaction mixture was further stirred for 6 hours. The lower phase was separated and dissolved in $CH_2Cl_2$. The $CH_2Cl_2$ phase was separated, and the aqueous phase was extracted with $CH_2Cl_2$. The $CH_2Cl_2$ extract was combined and washed with water. Vacuum degassing was carried out at 80° C. and 0.02 Torr for 24 hours, thereby obtaining an ionic liquid (0.90 g, 67.2%).

$^1$H NMR ($CD_3OD$, TMS, 500.2 MHz) δ 1.54 (t, J=7.5 Hz, 3H), 3.93 (s, 3H), 4.26 (q, J=7.5 Hz, 2H), 7.52 (s, 1H), 7.59 (s, 1H), 8.82 (s, 1H); $^{19}$F NMR ($CD_3OD$, $CFCl_3$, 470.6 MHz) δ −54.7 (t, J=11.1 Hz, 3F), −88.3 (s, 2F), −136.4 (m, 2F), −154.1 (q, J=40.0 Hz, 3F); $^{11}$B NMR ($CD_3OD$ $H_3BO_3$, 160.5 MHz) δ −19.8 (m, 1B); MS m/z (%) 111 (100) $[EMI]^+$, 253 (100) $[CF_3OCF_2CF_2BF_3]^-$; Anal Calcd. for $C_9H_{11}N_2F_{10}OB$: C, 29.70; H, 3.05; N, 7.70. Found: C, 29.60; H, 3.04; N, 8.00; Density: 1.478 g/mL; Specific conductivity: 9.10 mS/cm; Viscosity: 27.8 cP; Decomposition temperature: 286° C.

DEME $[CF_3OCF_2CF_2BF_3]$ (0.36 g, 65.5%)

DEME $[CF_3OCF_2CF_2BF_3]$ was obtained from $K[CF_3OCF_2CF_2BF_3]$ and a salt of DEME bromide in the same manner as described above. $^1$H NMR ($CD_3OD$, TMS, 500.2 MHz) δ 1.34 (t, J=7.3 Hz, 6H), 3.04 (s, 3H), 3.39 (s, 3H), 3.43 (q, J=7.3 Hz, 4H), 3.51 (t, J=4.5 Hz, 2H), 3.79 (m, 2H); $^{19}$F NMR ($CD_3OD$, $CFCl_3$, 470.6 MHz) δ −54.7 (m, 3F), −88.2 (s, 2F), −136.1 (q, J=18.2 Hz, 2F), −153.5 (q, J=40.0 Hz, 3F); $^{11}$B NMR ($CD_3OD$ $H_3BO_3$, 160.5 MHz) δ −19.6 (m, 1B); MS m/z (%) 146 (100) $[DEME]^+$, 253 (100) $[CF_3OCF_2CF_2BF_3]^-$; Anal Calcd. for $C_{11}H_{20}NF_{10}O_2B$: C, 33.11; H, 5.05; N, 3.51. Found: C, 33.11; H, 4.76; N, 3.78; Density: 1.40 g/mL; Specific conductivity: 2.5 mS/cm; Viscosity: 63 cP; Decomposition temperature: 312° C.

Additionally, N1224 [CF$_3$OCF$_2$CF$_2$BF$_3$] and Py13 [CF$_3$OCF$_2$CF$_2$BF$_3$] were obtained using N1224 and Py13 salts, respectively, in the same manner as described above.

Comparative Example 1

In place of K[CF$_3$OCF$_2$CF$_2$BF$_3$], K[CF$_3$CF$_2$CF$_2$CF$_2$BF$_3$], K[CF$_3$CF$_2$CF$_2$BF$_3$], K[BF$_4$], K[CF$_3$BF$_3$], or K[C$_2$F$_5$BF$_3$] was used in combination with Py13 bromide to obtain Py13 [CF$_3$CF$_2$CF$_2$CF$_2$BF$_3$], Py13 [CF$_3$CF$_2$CF$_2$BF$_3$], and Py13 [CF$_3$BF$_3$] in the same manner as described above.

EMI[CF$_3$CF$_2$CF$_2$CF$_2$BF$_3$], EMI[CF$_3$CF$_2$CF$_2$BF$_3$], EMI[BF$_4$], EMI[CF$_3$BF$_3$], EMI[C$_2$F$_5$BF$_3$], DEME[CF$_3$CF$_2$CF$_2$CF$_2$BF$_3$], DEME[CF$_3$CF$_2$CF$_2$BF$_3$], DEME[BF$_4$], DEME[CF$_3$BF$_3$], DEME[C$_2$F$_5$BF$_3$], N1224[CF$_3$CF$_2$CF$_2$CF$_2$BF$_3$], N1224[CF$_3$CF$_2$CF$_2$BF$_3$], N1224[BF$_4$], N1224[CF$_3$BF$_3$], N1224[C$_2$F$_5$BF$_3$], Py13[C$_2$F$_5$BF$_3$], and Py13 [BF$_4$] were synthesized according to Reference Documents 1 to 6.

Test Example 1

The electrical conductivity, viscosity, melting point, glass transition point, density, and decomposition temperature of each of the obtained salts were measured. The results are shown in Tables 1 to 5.

TABLE 1

Electrical conductivity at 25° C. (mS/cm)

| | [CF$_3$OCF$_2$CF$_2$BF$_3$]$^-$ | [CF$_3$CF$_2$CF$_2$BF$_3$]$^-$ | [CF$_3$CF$_2$CF$_2$CF$_2$BF$_3$]$^-$ | [BF$_4$]$^-$ | [CF$_3$BF$_3$]$^-$ | [C$_2$F$_5$BF$_3$]$^-$ |
|---|---|---|---|---|---|---|
| EMI | 9.1 | 8.6 | 5.2 | 13.6 | 14.8 | 12 |
| DEME | 2.5 | 1.9 | 1.3 | 1.3 | 3 | 3.2 |
| N1224 | 1.7 | Solid | Solid | Solid | 2.1 | 2.3 |
| Py13 | 4.2 | Solid | Solid | Solid | 5.0 | Solid |

TABLE 2

Viscosity at 25° C. (cP)

| | [CF$_3$OCF$_2$CF$_2$BF$_3$]$^-$ | [CF$_3$CF$_2$CF$_2$BF$_3$]$^-$ | [CF$_3$CF$_2$CF$_2$CF$_2$BF$_3$]$^-$ | [BF$_4$]$^-$ | [CF$_3$BF$_3$]$^-$ | [C$_2$F$_5$BF$_3$]$^-$ |
|---|---|---|---|---|---|---|
| EMI | 27.8 | 32 | 38 | 42 | 26 | 27 |
| DEME | 63.4 | 88 | 118 | 426 | 108 | 68 |
| N1224 | 101 | Solid | Solid | Solid | 210 | 104 |
| Py13 | 60.2 | Solid | Solid | Solid | 118 | Solid |

TABLE 3

Melting point (° C.)

| | [CF$_3$OCF$_2$CF$_2$BF$_3$]$^-$ | [CF$_3$CF$_2$CF$_2$BF$_3$]$^-$ | [CF$_3$CF$_2$CF$_2$CF$_2$BF$_3$]$^-$ | [BF$_4$]$^-$ | [CF$_3$BF$_3$]$^-$ | [C$_2$F$_5$BF$_3$]$^-$ |
|---|---|---|---|---|---|---|
| EMI | −30 | 8 | −4 | 15 | −20 | 1 |
| DEME | (−115) | (−112) | (−108) | 8 | −22 | (−113) |
| N1224 | 16 | 50 | 60 | 165 | −3 | 15 |
| Py13 | 25 | 79 | 77 | 64 | <25 | 63 |
| | | | | | Document 6 | Document 2 |

The numbers in parentheses indicate the glass transition temperatures of samples that only showed glass transition temperatures under the present measurement conditions.

TABLE 4

Density at 25° C. (g/mL)

| | [CF$_3$OCF$_2$CF$_2$BF$_3$]$^-$ | [CF$_3$CF$_2$CF$_2$BF$_3$]$^-$ | [CF$_3$CF$_2$CF$_2$CF$_2$BF$_3$]$^-$ | [BF$_4$]$^-$ | [CF$_3$BF$_3$]$^-$ | [C$_2$F$_5$BF$_3$]$^-$ |
|---|---|---|---|---|---|---|
| EMI | 1.48 | 1.49 | 1.55 | 1.28 | 1.35 | 1.42 |
| DEME | 1.40 | 1.37 | 1.42 | 1.2 | 1.25 | 1.31 |
| N1224 | 1.34 | Solid | Solid | Solid | 1.18 | 1.25 |
| Py13 | 1.43 | Solid | Solid | Solid | 1.27 | Solid |

TABLE 5

Decomposition temperature (° C.) at 10° C./min in a nitrogen flow; temperature at 10 wt % reduction

|      | $[CF_3OCF_2CF_2BF_3]^-$ | $[CF_3CF_2CF_2BF_3]^-$ | $[CF_3CF_2CF_2CF_2BF_3]^-$ | $[BF_4]^-$ | $[CF_3BF_3]^-$ | $[C_2F_5BF_3]^-$ |
|------|------|------|------|------|------|------|
| EMI   | 297 | 304 | 277 | 420 | 246 | 305 |
| DEME  | 312 | 275 | 287 | 372 | 174 | 322 |
| N1224 | 313 | 307 | 314 | 392 | 212 | 320 |
| Py13  | 324 | 323 | 329 | n.d. | 271 | 312 | n.d.: no data

The results of Table 1 revealed that the ionic liquids EMI [$CF_3OCF_2CF_2BF_3$], DEME[$CF_3OCF_2CF_2BF_3$], N1224 [$CF_3OCF_2CF_2BF_3$], and Py13[$CF_3OCF_2CF_2BF_3$] of the invention had lower viscosities and lower melting points, compared with corresponding conventional salts of [$CF_2CF_2CF_2CF_3BF_3$], [$CF_2CF_2CF_3BF_3$], [$BF_4$], [$CF_3BF_3$], and [$C_2F_5BF_3$], respectively. The electrical conductivity is high except for Py$_{13}$[$CF_3BF_3$].

The above results demonstrated that the ionic liquids EMI [$CF_3OCF_2CF_2BF_3$], DEME[$CF_3OCF_2CF_2BF_3$], N1224 [$CF_3OCF_2CF_2BF_3$], and Py13[$CF_3OCF_2CF_2BF_3$] of the invention have high electrical conductivities, low melting points, and low viscosities, and thus have excellent properties for use as electrochemical devices and solvents for organic reactions.

Reference Document 1: Z. B. Zhou, M. Takeda, M. Ue, J Fluorine Chem. 2003, 123, 127-131.
Reference Document 2: Z. B. Zhou, H. Matsumoto, K. Tatsumi, Chem. Lett. 2004, 33, 1636-1637.
Reference Document 3: Z. B. Zhou, H. Matsumoto, K. Tatsumi, Chem. Eur. J. 2004, 10, 6581-6591.
Reference Document 4: Z. B. Zhou, H. Matsumoto, K. Tatsumi, Chem. Eur. J. 2005, 11, 752-766.
Reference Document 5: Z. B. Zhou, H. Matsumoto, K. Tatsumi, Chem. Eur. J. 2006, 8, 2196-2212.
Reference Document 6: S. Forsyth, J. Golding, D. R. MacFarlane, M. Forsyth, Electrochim. Acta., 2001, 46, 1753-1757.

The invention claimed is:

1. An anion represented by [$CF_3OCF_2CF_2BF_3$]$^-$ for use in the production of ionic liquids.

2. An ionic liquid comprising an anion represented by [$CF_3OCF_2CF_2BF_3$]$^-$ and at least one organic onium ion.

3. A lithium battery comprising the ionic liquid according to claim 2.

4. An electric double-layer capacitor comprising the ionic liquid according to claim 2.

5. A method of producing an ionic liquid, comprising mixing a compound containing [$CF_3OCF_2CF_2BF_3$)]$^-$ as an anion component, with a compound containing at least one organic onium compound.

6. A salt comprising an anion represented by [$CF_3OCF_2CF_2BF_3$)]$^-$ and a cationic component.

7. The salt according to claim 6, wherein the cationic component is an alkali metal ion, an alkaline-earth metal ion, H$^+$, or Bu$_3$Sn$^+$.

8. The ionic liquid of claim 2, further comprising a cationic component.

9. The ionic liquid of claim 8, further comprising wherein the cationic component is an alkali metal ion, an alkaline-earth metal ion, H$^+$, or Bu$_3$Sn$^+$.

10. A lithium battery comprising the ionic liquid according to claim 8.

11. A lithium battery comprising the ionic liquid according to claim 9.

12. An electric double-layer capacitor comprising the ionic liquid according to claim 9.

13. An electric double-layer capacitor comprising the ionic liquid according to claim 9.

* * * * *